United States Patent [19]

Teuerstein et al.

[11] Patent Number: 4,606,852

[45] Date of Patent: Aug. 19, 1986

[54] FLAME RETARDANT POLYMER COMPOSITIONS

[75] Inventors: Avraham Teuerstein, Omer; Michael Rumack; Shaul Yanai, both of Beer-Sheva, all of Israel

[73] Assignee: Bromine Compounds Ltd., Beer-Sheva, Israel

[21] Appl. No.: 689,838

[22] Filed: Jan. 9, 1985

[30] Foreign Application Priority Data

Feb. 29, 1984 [IL] Israel .................................. 71108

[51] Int. Cl.$^4$ .................... C09K 21/08; C07C 137/00
[52] U.S. Cl. .................................. 252/609; 252/601; 558/59; 428/920
[58] Field of Search ............... 252/609, 601, 603; 260/456 NS; 428/921, 920

[56] References Cited

U.S. PATENT DOCUMENTS

| | | | |
|---|---|---|---|
| 3,873,451 | 3/1975 | Cumbo et al. | 252/609 |
| 3,925,335 | 12/1975 | Kuehn | 260/859 R |
| 4,175,072 | 11/1979 | Parr et al. | 528/299 |
| 4,301,058 | 11/1981 | Neukirchen et al. | 252/609 |
| 4,367,315 | 1/1983 | Zwaenepoel et al. | 525/169 |
| 4,377,506 | 3/1983 | Sprague | 252/609 |

*Primary Examiner*—Stephen J. Lechert, Jr.
*Assistant Examiner*—Howard J. Locker
*Attorney, Agent, or Firm*—Frishauf, Holtz, Goodman & Woodward

[57] ABSTRACT

Normally flammable organic polymers are rendered flame retardant by the incorporation of compounds corresponding to the formula:

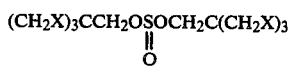

wherein each X is independently Br or Cl. The normally flammable organic polymers are selected from polyolefin, such as polypropylene, epoxy resins, unsaturated polyesters and styrene-based resins. The sulfite ester of tribromo neopentyl alcohol is preferred.

15 Claims, No Drawings

FLAME RETARDANT POLYMER COMPOSITIONS

The present invention relates to flame retardant polymer compositions. More particularly, the invention relates to flame retardant polymer compositions containing as flame retardant reagents, sulfite esters of halogenated neopentyl alcohol.

In co-pending Patent Application Ser. No. 689,837 filed Jan. 9, 1985 there were disclosed new compounds of sulfite esters of halogenated neopentyl alcohol having the general formula:

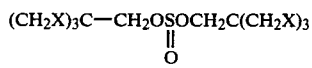

wherein each X is independently Br or Cl.

It has now been found that the above compounds posses an outstanding fire retardant property for polymeric materials in general and polyolefins in particular.

Thus, with an amount of less than eight parts of the new halogenated neopentyl sulfite esters per 100 parts polypropylene, which corresponds to less than 5% halogen, a self-extinguishing polypropylene is obtained. This is quite remarkably since tribromoneopentyl alcohol by itself, which contains 73.8% by weight bromine (compared with 68.9% of the sulfite ester according to the present invention) imparts only a poor fire retardant property for polypropylene. The amount of the reagent is generally in the range of 3–20 parts per 100 parts of polypropylene. As encountered in the flame retardants technique, the incorporation of antimony oxide may further enhance the flame retardant property of the new compounds. Generally the amount of antimony oxide will be in the range of between 1 to 20 parts per 100 parts of polymer. Additionally, the polymer may include conventional additives such as: colorants, weather-proofing agents (ultraviolet ray absorbing agents), antistatic agents or other flame-retardant agents, without deteriorating its flame retardant property imparted by the new sulfite esters of halogenated neopentyl alcohol according to the present invention.

The improved flame retardant property of the sulfite esters of halogenated neopentyl alcohol compared to the starting reagent (brominated neopentyl alcohol), may be explained by the particular improved processability resulted by the compatibility of the reagent with the polymeric material. It also appears that the incorporation of these compounds to the polypropylene has only a little effect on the physical properties of the olefin. While the invention covering the above compounds has been described with specific embodiments thereof, it will be understood that it is capable of further modifications and this patent is intended to cover any variation, uses or adaptations of the invention and including such departures from the present disclosure as come within known or customary practice in the art to which the invention pertains and as may be applied to the essential features hereinbefore set forth and as fall within the scope of the invention.

In order to further illustrate the nature of this invention and the manner of practising it, the following Examples are presented for clearness for understanding only and no limitation should be understood therefrom.

In the Examples the percentages given are by weight unless otherwise stated.

EXAMPLE 1

The sulfite ester of tribromo neopentyl alcohol (as prepared in Example 1, of co-pending Patent Application Ser. No. 689,837) was tested as flame retardant for polypropylene (type M12, produced by AMOCO). At the same time three other samples of the same polymer were also tested: two with addition of antimony oxide at two levels, and one with N,N'-alkylene-bis-tetrahalophthalimide (designated as BT-93) known as a fire retardant for polypropylene. The results obtained are summarized in the following Table 1.

TABLE 1

| | Results on fire retardant properties imparted to polypropylene. | | | | | | | |
|---|---|---|---|---|---|---|---|---|
| | amounts in phr | | | | | | Results on fire retardancy | |
| Exper. Number | Polypropylene | BT-93 | SHN | Antimony oxide | Ca-Stearate | % Br (by wt) | Rate | LOI |
| 1 | 100 | — | 7.7 | 4.0 | 1.0 | 4.7 | $V_2$ | |
| 2 | 100 | — | 9.6 | 5.0 | 1.0 | 5.7 | $V_2$ | 26 |
| 3 | 100 | — | 17 | — | — | 10 | $V_2$ | |
| 4 | 100 | 10 | — | 5.0 | 1.0 | 5.7 | fails | 22 |

The above results clearly show the improved fire retardant property imparted to the polypropylene, even with a small amount of the reagent sulfite ester of tribromoneopentyl alcohol corresponding to 4.7% $Br_2$. Experiment 4 shows that using a well-known fire retardant such as BT-93, at a level corresponding to 5.7% $Br_2$, a poor fire retardancy property was obtained with a LOI of only 22. By increasing the amount of the reagent, no Ca-Stearate (as plasticizer) seems to be required due to the compatibility of the reagent with the polypropylene.

EXAMPLE 2

The sulfite ester of tribromo neopentyl alcohol (SHN), was tested as flame retardant additive in two thermosetting polymers: (a) Epoxy resin and (b) unsaturated polyester. The formulations and flammability performances with the above polymers are summarized in the following Table 2.

TABLE 2

| Flame retardancy of SHN in epoxy resin[a] and unsaturated polyester resin[b]. | | | | | | |
|---|---|---|---|---|---|---|
| Exp. No | % Br by wt. | Epoxy Resin[a] | | SHN[c] | U PE RESIN[b] | LOI |
| | | Resin | Hardener | | | |
| 1 | — | 15.2 g | 2.8 g | — | — | 22.2 |
| 2 | 6.7 | 15.2 g | 2.8 g | 2 g | — | 26.3 |
| 3 | — | — | — | — | 15 g | 18.6 |
| 4 | 7.6 | — | — | 1.95 g | 15 g | 21.5 |

[a]Epoxy coating "308" (produced by Tambour, Israel).
[b]Unsaturated polyester Merporal 555 (Trade Mark, produced by Mackteshim Chemical Works, Israel).
[c]Sulfite ester or tribromoneopentyl alcohol.

The above flammability results as measured by LOI values are in the range expected by the percentage of the halogen incorporated in the resin.

EXAMPLE 3

The sulfite ester of tribromoneopentyl alcohol (SHN) can render also V-o formulations in polypropylene in conjunction with customary additives for this purpose.

V-o formulations using the SHN fire retardant reagent are summarized in the following Table 3.

TABLE 3

V-o formulations in 3.2 mm samples of polypropylene.

| Exp. No. | Polypr.[a] (g) | $(NH_4)_2SO_4$ (g) | Silica[b] (g) | Talc (g) | SHN (g) | A.O.[c] (g) | $Br_2$ % |
|---|---|---|---|---|---|---|---|
| 1 | 47 | 15 | 20 | — | 11.6 | 5.8 | 8 |
| 2 | 77.5 | — | — | — | 15 | 7.5 | 10 |
| 3 | 75 | — | — | 10 | 10 | 5 | 6.9 |

[a]polypropylene produced by Amoco MI2;
[b]silica-Extrusil;
[c]A.O. - Antimony oxide.

EXAMPLE 4

The sulfite ester of tribromoneopentyl alcohol (SHN) renders V-o performances in styrene-based resins turning the black characteristic smoke of these resins into a light white smoke. Typical formulations are given in the following Table 4.

TABLE 4

Burning characteristics of SHN in styrene - based resins (3.2 mm samples).

| Exp. No. | Resin | SHN (% by wt) | A.O.[a] (% by wt) | Bromine (% by wt) | UL94 |
|---|---|---|---|---|---|
| 1 | ABS[b] | 8.8 | 4.3 | 6 | V-2 |
| 2 | ABS | 17.6 | 8.6 | 12 | V-O |
| 3 | HIPS[c] | 8.8 | 3.7 | 6 | V-2 |
| 4 | HIPS | 17.6 | 7.4 | 12 | V-2 |

[a]antimony oxide.
[b]acrylonitrile - butadiene-styrene.
[c]high-impact polystyrene.

EXAMPLE 5

The sulfite ester of tribromoneopentyl alcohol (SHN) was also found to be suitable as fire retardant in poly-(ethylene-block-propylene). Typical formulations are given in the following Table 5.

TABLE 5

V-2 formulations containing SHN with 3.2 mm samples of polyethylene-block-propylene[a].

| Exp. No. | SHN (% by wt) | AO[b] (% by wt) | Bromine (% by wt) | Atomic ratio Br/Sb | Burning time[c] (sec) |
|---|---|---|---|---|---|
| 1 | 8.8 | 1.9 | 6 | 6 | 18 |
| 2 | 8.8 | 3.7 | 6 | 3 | 20 |
| 3 | 4.4 | 1.9 | 3 | 3 | 119 |

[a]100 g polyethylene-block-propylene. (Lacqtene, p 3120, MN4-Trade Mark, produced by ATOCHEM).
[b]antimony oxide.
[c]according to UL94.

We claim:
1. A flame retarded composition comprising a normally flammable organic polymer and a flame retardant reagent having the formula:

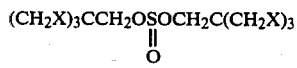

wherein each X is independently Br or Cl.

2. The composition according to claim 1, containing an amount of 1 to 20 parts by wt. antimony trioxide per 100 parts of a normally flammable polymer.

3. The composition according to claim 1, wherein the normally flammable organic polymer is polypropylene.

4. The composition according to claim 1, wherein the normally flammable organic polymer is epoxy resin.

5. The composition according to claim 1, wherein the normally flammable organic polymer is unsaturated polyester.

6. The composition according to claim 1, wherein the normally flammable organic polymer is styrene-based resins.

7. The composition according to claim 1, wherein the normally flammable organic polymer is poly(ethylene-block-propylene).

8. The composition according to claim 3, containing between 3 and 20 parts of the flame retardant reagent per 100 parts of polypropylene.

9. The composition according to claim 1, wherein said flame retardant regent is the sulfite ester of tribromo neopentyl alcohol.

10. The composition according to claim 2, wherein said organic polymer is polypropylene and the composition contains between 3 and 20 parts of the sulfite ester of tribromo neopentyl alcohol as said flame retardant reagent per 100 parts of polypropylene.

11. The composition according to claim 8, wherein said flame retardant reagent is the sulfite ester of tribromo neopentyl alcohol.

12. The composition according to claim 4, wherein said flame retardant reagent is the sulfite ester of tribromo neopentyl alcohol.

13. The composition according to claim 5, wherein said flame retardant reagent is the sulfite ester of tribromo neopentyl alcohol.

14. The composition according to claim 6, wherein said flame retardant reagent is the sulfite ester of tribromo neopentyl alcohol.

15. The composition according to claim 7, wherein said flame retardant reagent is the sulfite ester of tribromo neopentyl alcohol.